United States Patent
Hecker et al.

(10) Patent No.: US 6,595,214 B1
(45) Date of Patent: *Jul. 22, 2003

(54) NASAL RESPIRATION MASK

(75) Inventors: Karl-Heinz Hecker, Aschau (DE); Rudolf Schinagl, Unterhaching (DE)

(73) Assignee: MPV-Truma Gesellschaft fur (DE)

( * ) Notice: Subject to any disclaimer, the term of this patent is extended or adjusted under 35 U.S.C. 154(b) by 18 days.

This patent is subject to a terminal disclaimer.

(21) Appl. No.: 09/718,598

(22) Filed: Nov. 22, 2000

(51) Int. Cl.7 .............................. A62B 18/02
(52) U.S. Cl. ...................... 128/207.13; 128/206.21
(58) Field of Search ............. 128/201.22–201.25, 128/201.28, 205.25, 205.27, 205.28, 206.12–206.15, 206.17–206.19, 206.21, 206.24, 206.26–206.28, 207.111, 207.12, 207.13, 200.28

(56) References Cited

U.S. PATENT DOCUMENTS

| | | | | |
|---|---|---|---|---|
| 1,081,745 A | * | 12/1913 | Johnston et al. | 128/203.25 |
| 1,176,886 A | * | 3/1916 | Ermold | 128/203.25 |
| 4,944,310 A | * | 7/1990 | Sullivan | 128/205.25 |
| 5,117,819 A | * | 6/1992 | Servidio et al. | 128/204.18 |
| 5,570,689 A | * | 11/1996 | Starr et al. | 128/206.24 |
| 5,662,101 A | * | 9/1997 | Ogden et al. | 128/202.27 |
| 5,687,715 A | * | 11/1997 | Landis et al. | 128/204.18 |
| 6,044,844 A | * | 4/2000 | Kwok et al. | 128/205.25 |
| 6,112,746 A | * | 9/2000 | Kwok et al. | 128/206.26 |
| 6,119,693 A | | 9/2000 | Kwok et al. | 128/207.11 |
| 6,123,071 A | * | 9/2000 | Berthon-Jones et al. | 128/204.18 |
| 6,192,886 B1 | * | 2/2001 | Rudolph | 128/205.25 |
| D439,326 S | * | 3/2001 | Hecker et al. | D24/110.1 |
| 6,427,694 B1 | * | 8/2002 | Hecker et al. | 128/206.21 |
| 6,463,931 B1 | * | 10/2002 | Kwok et al. | 128/207.11 |
| 6,467,483 B1 | * | 10/2002 | Kopacko et al. | 128/207.12 |
| 6,494,207 B1 | * | 12/2002 | Kwok | 128/207.11 |

FOREIGN PATENT DOCUMENTS

| | | | |
|---|---|---|---|
| DE | 19817332 | * | 4/1997 |
| EP | 0549299 | * | 12/1992 |
| WO | WO 99/65554 | | 12/1999 |

* cited by examiner

Primary Examiner—Weilun Lo
Assistant Examiner—Teena Mitchell
(74) Attorney, Agent, or Firm—Marshall, Gerstein & Borun

(57) ABSTRACT

A The invention relates to a nasal breathing mask having a mask part (1) and a mask-holding part (2) which at the upper end is connected to a tube (3), a forehead plate (10), which is connected to a forehead-plate mount (9), being axially adjustable on the elongate tube (3) by means of a latching/clamping connection.

17 Claims, 5 Drawing Sheets

NASAL RESPIRATION MASK

FIELD OF THE INVENTION

The invention generally relates to nasal breathing masks.

BACKGROUND OF THE INVENTION

Nasal breathing masks are used, inter alia, to supply respiratory air primarily for therapeutic purposes, such as for example for treating disturbed sleep accompanied by apnea.

Conventional breathing masks comprise a partially elastic mask part, which is suitably anatomically shaped to bear against the region of the mouth and/or nose of the patient, and a mask-holding part, which is connected to the mask part and to which holding straps of the breathing mask are attached, so that the mask can be pressed onto the nose and/or mouth, the holding straps being guided behind the back of the head. The respiratory air can be supplied through a breathing hose via a hose connection on the mask-holding part. The respiratory air is generally taken from a unit which generates superatmospheric pressure.

WO 99/65554, in the name of the applicant, has disclosed a nasal breathing mask having a mask part and a mask-holding part which is connected thereto and to at least one strap for positioning the breathing mask on the nose of a user and which at the top end is connected to an elongate tube, which in turn is connected to a hose connection for a breathing hose and on which a forehead plate, which is connected to a forehead-plate mount, is axially adjustable. In this mask, the forehead-plate mount has a sleeve which can be displaced in the axial direction on the elongate tube. In order, in this breathing mask which is known from the prior art, on the one hand to ensure that the axial adjustability is possible, so that the distance between the forehead plate and the mask part can be adapted as a function of the anatomy of the user, and, on the other hand, to maintain the axial height of the forehead plate which is then set if the patient moves while sleeping, grooves which run around the inner surface of the sleeve are provided, into which grooves corresponding O-rings are inserted. To simultaneously achieve easy adjustability and nevertheless a secure position, a slight surface pressure between the groove of the sleeve, the O-ring mounted therein and the tube is advantageous.

To achieve a slight surface pressure, however, relatively thick O-rings are required, for which purpose in turn relatively large grooves are required in the sleeve. However, such grooves cannot be produced by means of collapsible cores during the injection-molding operation, since, for production and design reasons, such cords cannot be made large enough.

However, the use of relatively small O-rings has the associated drawback that, in constant use, they tend to migrate out of the groove in the sleeve, so that as a result the easy adjustability is lost and the secure position of the axial height which has been set is also not ensured when the breathing mask is being used while the user is asleep. Having to constantly thread the O-rings back in for reuse leads to a considerable reduction in the operating comfort of a breathing mask of this type.

SUMMARY OF THE INVENTION

Working on the basis of these drawbacks which are known from the prior art, the present invention is based on the object of providing a nasal breathing mask of the generic type which ensures that it is held securely and functions perfectly even for users who sleep restlessly, which provides minimum possible restriction to the freedom of movement of the user and which makes adjusting the distance between the forehead plate and the mask part in order to adapt to the anatomy of the user firstly easy to manage and secondly securely positioned after it has been set.

According to the invention, this object is achieved by means of a breathing mask as claimed herein.

Advantageous configurations of the breathing mask according to the invention are given in the dependent claims.

The nasal breathing mask according to the invention offers the advantage that ease of handling during the axial adjustment of the forehead-plate mount on the tube is ensured, so that the distance between the forehead-plate and the mask part can be individually adapted to every patient and the anatomy of every patient.

At the same time, the latching or clamping mechanism between the forehead-plate mount and the tube ensures that, once set, the axial height of the forehead plate can no longer change.

In a preferred embodiment, the forehead-plate mount is designed in the manner of a U-shaped collar. This collar is open toward the front, i.e. in the side remote from the user, and has recesses on the inside which run parallel to one another in the axial direction and annularly in the circumferential direction.

Annularly encircling ribs, which are of complementary design with respect to the recesses, are formed integrally on the circumferential surface of the tube, so that they can be pushed releasably into the recesses. The engagement between the recesses and the ribs, which are preferably in each case arranged equidistantly, provides the possibility of axially securing the forehead-plate mount with respect to the tube at the fixed distances between the recesses and the ribs.

The collar advantageously has an internal diameter which is slightly smaller than the external diameter of the ribbed tube, so that the forehead-plate mount can be latched onto the tube in a releasable manner. This undersizing alone allows a sufficient latching connection between these two components, so that initial secure positioning is provided when the distance between the forehead plate and the mask part is being adapted.

When the axial height which is to be set has been determined as a function of the anatomy of the patient, the position of the device can be finally fixed securely as a result of the possibility of a latching clip, on the side of the forehead-plate mount opposite from the user, being latchable onto the forehead-plate mount in a releasable manner.

According to an advantageous configuration of the invention, the latching clip has two limbs which are under a prestress. At their respective ends, the limbs are provided with a lug which can engage into an opening arranged in the forehead plate. This latching into place is effected by pressing the limbs together, against the prestress, introducing the lugs into the respective openings, so that then the prestress allows the lugs to latch into the openings.

According to another advantageous configuration of the invention, the latching clip also has ribs on its inner side toward the user, i.e. toward the tube, which ribs can be received in a complementary manner in the spaces which are formed by the ribs of the tube, so that in this respect too a sufficiently secure position is provided.

The latching clip clamps the tube against the forehead-plate mount and prevents the possibility of this mount unintentionally becoming detached while the user is asleep.

To facilitate the introduction of the limbs into the openings in the forehead plate, the limbs can be received in guides which are formed on the outer flanks of the U-shaped collar of the forehead-plate mount.

To prevent the possibility of the tube twisting radially in the forehead-plate mount, according to the invention the forehead-plate mount may, on the opposite side from its opening, have a groove which runs in the axial direction and in which a corresponding axial rib which is formed integrally on the tube can be received axially.

In an advantageous configuration of the invention, the forehead-plate mount and the forehead plate may be of integral design.

According to another advantageous configuration of the invention, between the mask part and the forehead plate there is provided a region of the tube which is designed and arranged in such a way that the mask part can be moved toward the user with respect to the forehead-plate mount. An inventive design of the tube of this type provides a further possibility of adjustment with respect to the varying anatomies of the patients, so that the distance between the forehead and the nose in the frontal plane of the patient can be compensated for. A region of this type may, for example, be of flexible design and consist in a reduction in the wall thickness of the tube, so that a greater degree of flexibility, in particular flexural elasticity, is offered compared to the remaining tube body of greater wall thickness.

According to the invention, this region can also be produced by means of at least one ball joint, preferably by means of two ball joints, so that the mask part can be moved toward the nose of the user, with two degrees of freedom being created by the ball joints.

Another design according to the invention can be effected by configuring the more flexible region in the form of bellows, in the manner of a bendable drinking straw.

According to an advantageous configuration of the invention, a flexible, in particular flexurally elastic, hose is arranged between the mask-holding part and the tube. Advantageously, a tube connection piece, over which, as also over the tube, the hose can be pushed, is formed integrally on the mask-holding part. In this case, it is advantageous if both the tube connection piece and the tube have a circumferential sealing lip or a sealing bead, over which the hose can be pushed so as to form a connection which can be released again but is sufficiently airtight and rigid.

When using a flexible hose, according to the invention a distance between the tube connection piece of the mask-holding part and the tube of a few millimeters, for example of 2 mm, is sufficient to provide sufficient mobility to compensate for the anatomies which exist.

On account of the hygiene and cleanability which have to be considered with a nasal breathing mask of this type, according to a further advantageous configuration of the invention all the components of the breathing mask are made from silicone.

BRIEF DESCRIPTION OF THE DRAWINGS

Further advantages and advantageous configurations of the invention are given in the following description in conjunction with the drawing, in which.

DETAILED DESCRIPTION

Figure 1:
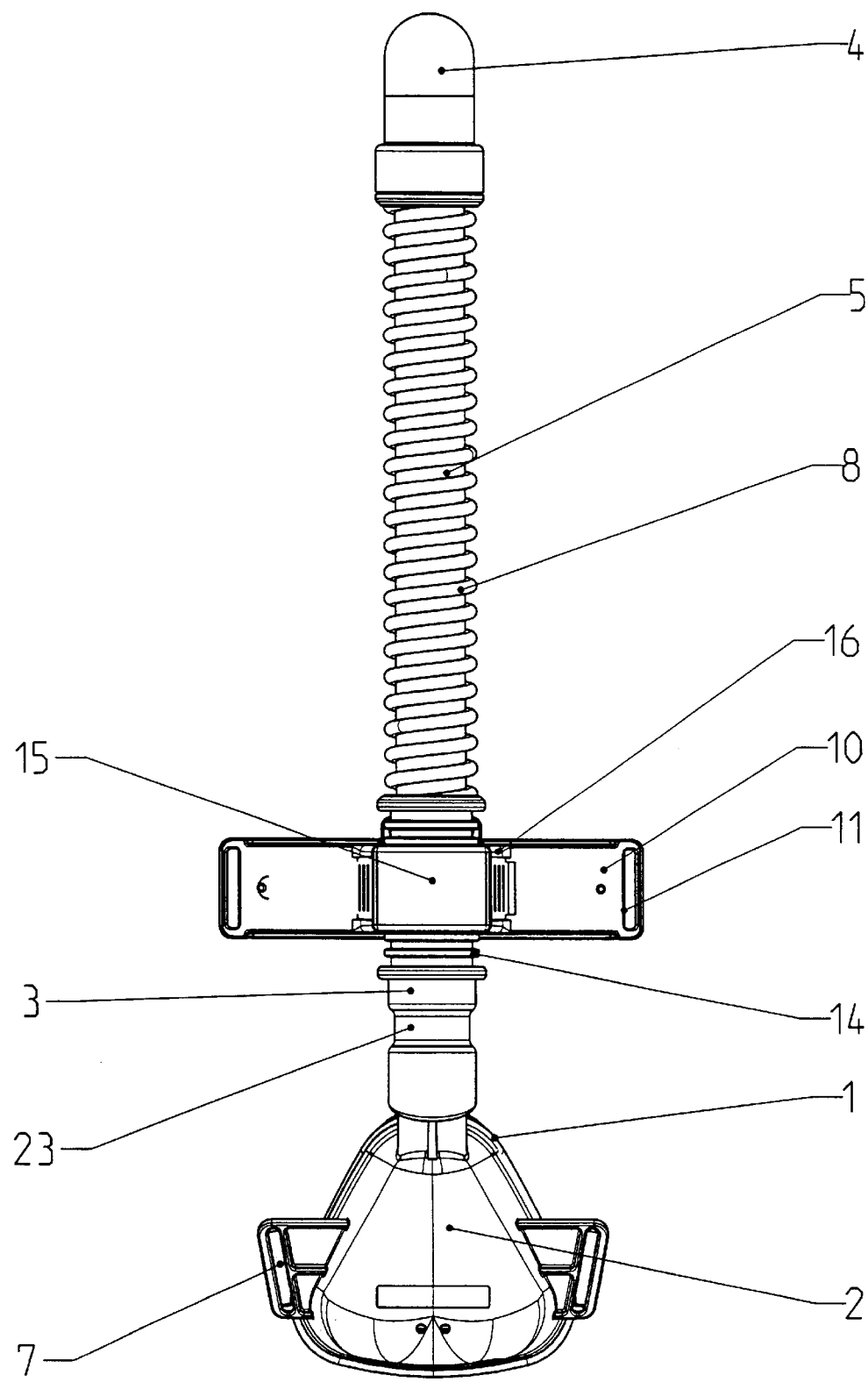
FIG. 1 shows a frontal view of the nasal breathing mask according to the present invention.
Figure 2:
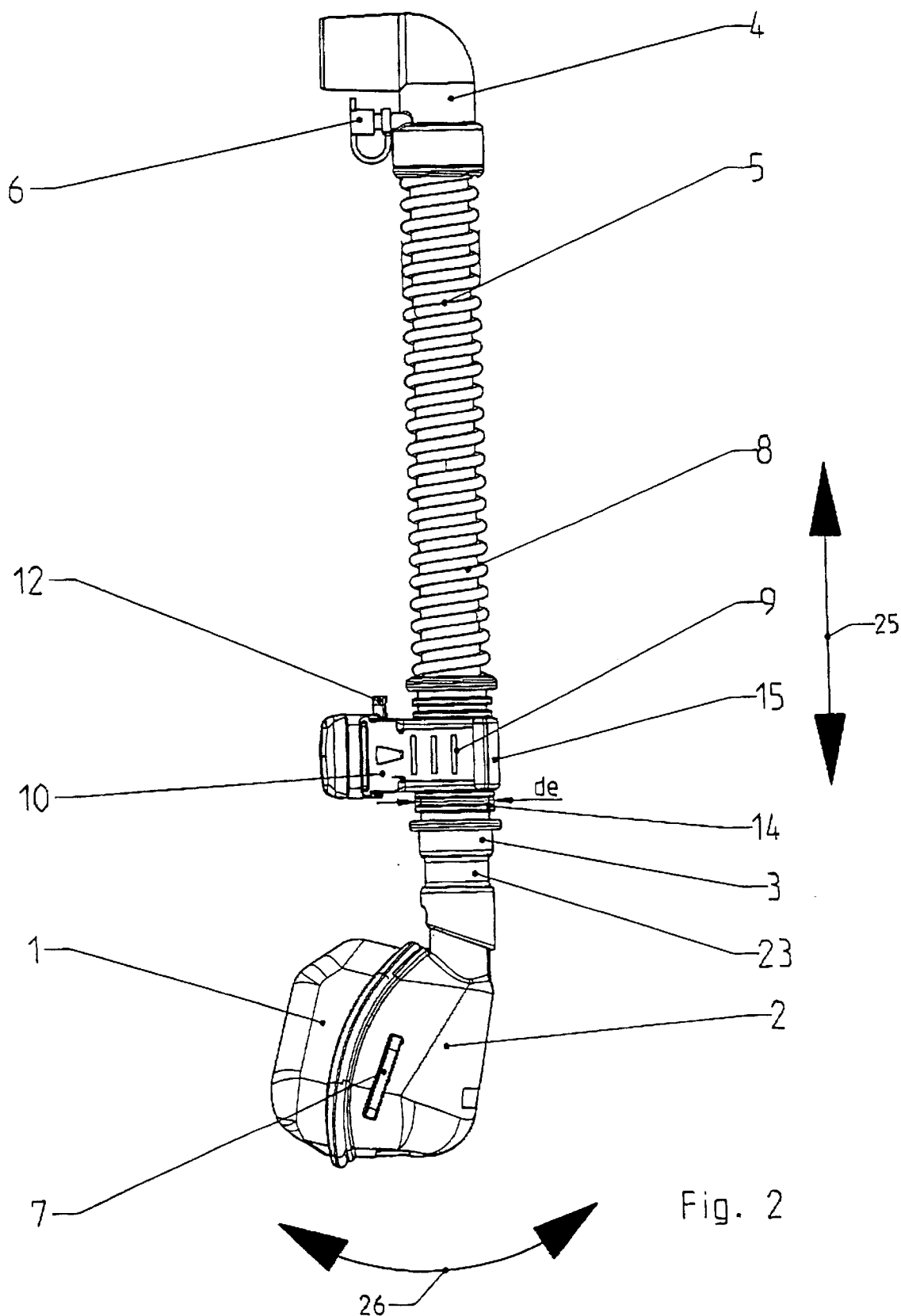
FIG. 2 shows a side view of the breathing mask shown in FIG. 1.

The embodiment of a nasal breathing mask according to the present invention which is shown in FIG. 1 and FIG. 2 comprises a flexible mask part 1 for adapting the breathing mask to the anatomy of the patient. The flexible and deformable mask part 1 is releasably connected to the mask-holding part 2, for example as a result of an integrally formed bead of the elastic and deformable mask part 1 being latched into an annular cutout in the mask-holding part 2, so that by the possibility of simply changing and cleaning the mask part 1, it is possible for the use of this nasal breathing mask to be hygienically switched between a plurality of patients. Furthermore, to adapt the mask to the different facial shapes and nose sizes of the patients, it is possible to use differently shaped and sized elastic mask parts 1.

An elongate tube 3 is arranged, substantially vertically, on the mask-holding part 2.

A flexurally elastic intermediate hose 5 is provided between the elongate tube 3 and the angle tube 4, so that the wearing comfort for the user is increased. In this way, the angle tube 4, which is used for the connection of a breathing hose (not shown), is positioned on the top of the head and completely out of the way of the region of the user's face, making the breathing mask easier to manage, in particular when connecting the breathing hose to the angle tube 4. Furthermore, in this way the forces acting on the breathing mask are decoupled further, since impacts, transverse forces and the like acting on the breathing hose as a result of the patient moving while asleep can additionally be absorbed by the flexurally elastic intermediate hose 5.

Closeable connection pieces 6 for supplying and/or removing gas to or from the respiration air flowing to the mask part 1 are provided on the angle tube 4. In this way it is possible, for example, to carry out measurements in the respiratory air or to introduce additives to the respiratory air, for example gaseous anesthetics, without it being necessary for additional disruptive lines to be arranged in the region of the patient's face.

On the mask part 1 there are eyelets 7 for securing a strap in order to offer additional protection against undesirable slipping.

On its outer side, the intermediate hose 5 has a ribbed surface, and on its inner side it has a smooth surface, so that on the one hand it is of flexurally elastic design, but on the other hand it is secured against being pushed off and becoming squeezed undesirably. The flexural elasticity prevents cracks when the intermediate hose 5 is constantly reused and also prevents it from breaking. The smooth surface on the inner side of the intermediate hose 5 ensures unimpeded flow of respiratory air, so that turbulence within the airstream is as far as possible prevented. The ribbed surface of the outer side is brought about by a helically running cord 8 which is positively locked to the smooth outer side of the intermediate hose 5.

According to the invention, a forehead-plate mount 9 is arranged between the stops of the mask-holding part 2 and the intermediate hose 5 on the elongate tube 3. In the exemplary embodiment shown, the forehead-plate mount 9 is integrally connected to the forehead plate 10.

Straps are attached to the forehead plate 10 by means of eyelets 11 and 12, which straps are guided over the head in order for the nasal breathing mask to be held more stably.

The nasal breathing mask is positioned by pulling the entire unit over the head of the patient. In the process, the optimum distance between the forehead plate 10 and the mask part 1, which is a result of the anatomy of the user, i.e. of the distance between the forehead and the nose, is fixed by an axial adjustment of the forehead-plate mount 9 on the elongate tube 3. The axial direction is indicated by arrow 25 in FIG. 2.

Figure 3:
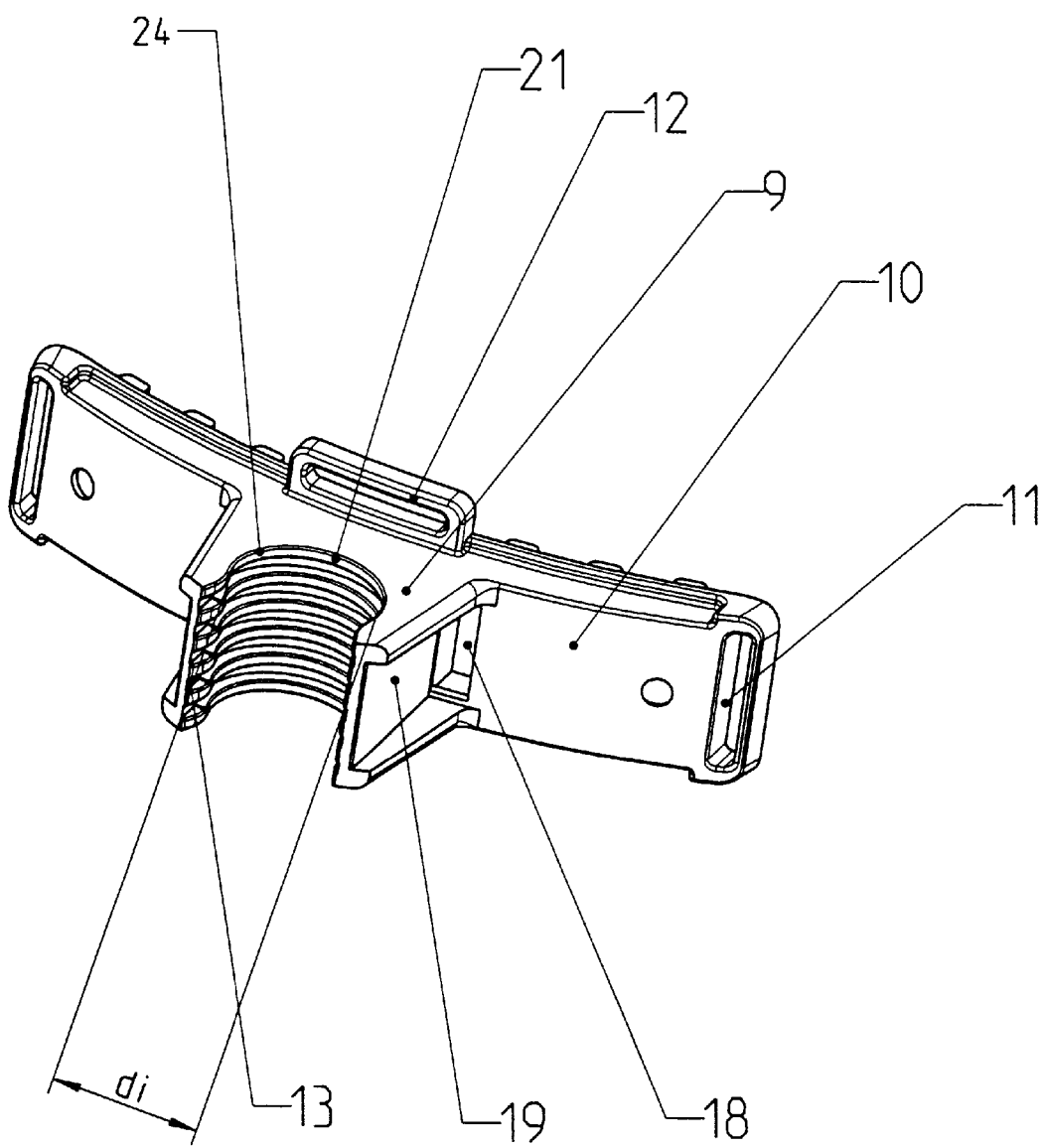
FIG. 3 shows a perspective view of the forehead-plate mount and the forehead plate according to the present invention.
Figure 4:
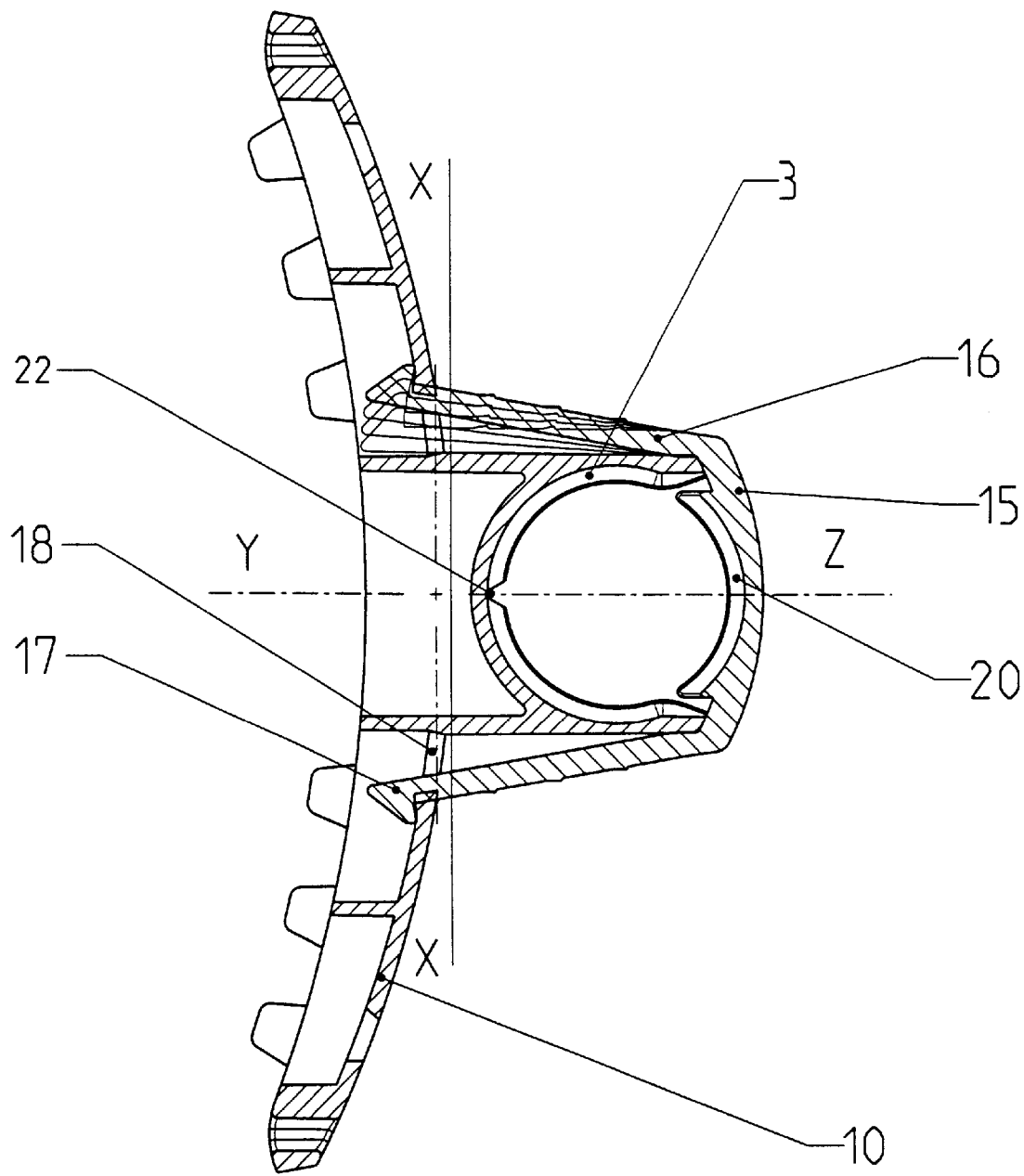
FIG. 4 shows a section through the forehead-plate mount and the forehead plate with a latched-on latching clip according to the present invention.
Figure 5:
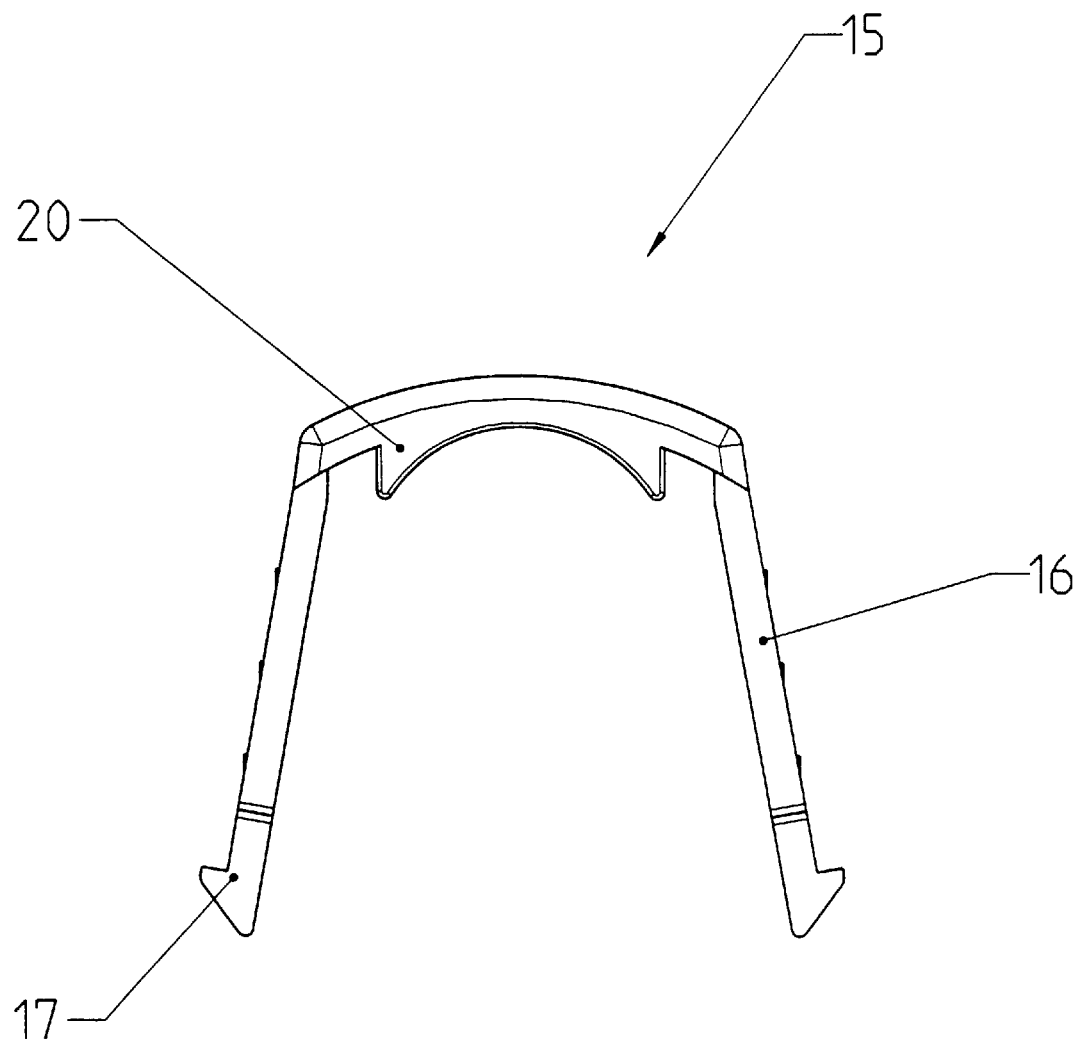
FIG. 5 shows a plan view of the latching clip.

The axial setting is effected by means of a latching/clamping connection between the elongate tube 3 and the forehead-plate mount 9, as becomes clear from FIGS. 3 to 5.

FIG. 3 shows a perspective view of the forehead-plate mount 9 and the forehead plate 10, which in the present exemplary embodiment are of integral design. As can be seen, the forehead-plate mount 9 extends in the form of a U-shaped collar 24 which is open toward the front. The inner surface of the collar has recesses 13 which run parallel to one another in the axial direction and annularly in the circumferential direction, at regular intervals. Complementary, annular ribs 14, which are formed integrally on the circumferential surface of the elongate tube, as shown in FIGS. 1 and 2, can be releasably inserted into these recesses 13.

It can be seen that, as a result of recesses 13 being formed in the forehead-plate mount 9, on the one hand, and ribs 14 being formed on the tube 3, on the other hand, the axial height or the distance between the forehead-plate mount 9 and the mask part 1 can be individually fixed, as indicated by the arrow 25 in FIG. 2, by engagement or meshing.

To provide the tube 3 with a certain positional security during positioning, the collar has an internal diameter "di" which is slightly smaller than the external diameter "de" of the tube 3, so that the forehead-plate mount 9 can be latched onto the tube 3 in a releasable manner.

After the final axial height has been determined, the overall arrangement can be fixed as a result of the fact that, according to the invention, a latching clip 15 can be latched at the front side onto the forehead-plate mount 9 in a releasable manner, as illustrated in FIG. 4.

FIG. 5 shows a view of the latching clip 15. It has two limbs 16 which are under a prestress and each have a lug 17 at their end.

As shown in FIG. 4, the lugs 17 each engage in an opening 18 provided in the forehead plate 10 and, on account of the prestress of the limbs 16, latch behind this opening. As a result of the limbs 16 being pressed together, counter to the prestress, the latching clip 15 is extremely easy to release again at any time.

To make it easier for the latching clip 15 to latch onto the forehead-plate mount 9, the latter has guides 19, into which the limbs 16 can be slideably guided, on the outer flanks of its U-shaped collar.

According to the invention, to provide additional axial fixing of the position of the tube 3, the latching clip 15 has, on its inner side, i.e. toward the user, ribs 20 which are received in a complementary manner in the spaces formed by the ribs 14 of the tube 3, so that the ultimate result is a connection between the tube 3 and the forehead-plate mount 9 which is completely rigid but can be released again.

To prevent a radial twisting movement of the tube 3 inside the collar of the forehead-plate mount 9, an axially running groove 21, which is situated on the opposite side of the forehead-plate mount 9 from the opening of the collar, is arranged in the forehead-plate mount 9. A corresponding, complementary rib 22, which is formed integrally and axially on the tube 3, can be received in this groove 21.

According to another advantageous configuration of the invention, along the tube 3, as shown in FIGS. 1 and 2, there is a region 23 which is designed to be more flexible than the remainder of the tube body and is arranged along the tube 3 in such a way that the mask part 1 can be moved toward the user with respect to the forehead-plate mount 9, as indicated by the bottom arrow 26 in FIG. 2. A more flexible region 23 of this type can be produced, for example, by reducing the wall thickness of the tube 3 as a function of the material in such a way that this region 23 has an increased flexural elasticity compared to the remainder of the tube 3. In this way, it is possible to compensate for the distance between the forehead and the nose in the frontal plane of the patient.

What is claimed is:

1. A nasal breathing mask comprising:
   a mask part;
   a mask-holding part adapted to receive at least one strap for positioning the mask part on a nose of a user;
   a tube extending in an axial direction and having a first end connected to a top end of the mask-holding part and a second end, the tube defining an external surface;
   a breathing hose having a hose connection attached to the tube second end;
   a forehead-plate mount having an internal surface complementary with the tube external surface to create a positive engagement between the forehead-plate mount and the tube, wherein the positive engagement is releasable to allow adjustment of the forehead-plate mount in the axial direction; and
   a forehead plate connected to the forehead-plate mount.

2. The nasal breathing mask of claim 1, in which a side of the forehead-plate mount remote from the user includes a substantially U-shaped collar having an open end extending away from the user, an inside of the collar having recesses extending parallel to one another in the axial direction and annularly in a circumferential direction to define the internal surface, and in which the tube external surface is formed with annular ribs sized for releasable insertion into the recesses.

3. The nasal breathing mask of claim 2, in which the collar has an internal diameter that is slightly smaller than an external diameter of the tube, so that the forehead-plate mount is releasably latchable onto the tube.

4. The nasal breathing mask of claim 2, in which the recesses and ribs are arranged equidistantly in the axial direction.

5. The nasal breathing mask of claim 2, further comprising a latching clip adapted to releasably latch onto a side of the forehead-plate mount remote from the user.

6. The nasal breathing mask of claim 5, in which the latching clip includes two prestressed limbs, an end of each limb having a lug, and in which the forehead plate includes openings sized to receive the lugs such that the prestressed limbs releasably latch the lugs behind the openings.

7. The nasal breathing mask of claim 6, in which a side of the latching clip facing the user includes ribs adapted for insertion into spaces formed between adjacent ribs of the tube.

8. The nasal breathing mask of claim 5, in which an outside of the collar is formed with guides sized to receive the limbs of the latching clip.

9. The nasal breathing mask of claim 1, in which the tube includes an axially extending rib and the forehead-plate mount includes an axially extending groove sized to receive the axially extending tube rib.

10. The nasal breathing mask of claim 1, in which the forehead-plate mount is formed integrally with the forehead plate.

11. The nasal breathing mask of claim 1, in which the tube includes a flexible region positioned between the mask-holding part and the forehead-plate mount so that the mask part is movable toward the user with respect to the forehead-plate mount.

12. The nasal breathing mask of claim 11, in which the flexible region of the tube includes at least one ball joint or bellows.

13. The nasal breathing mask of claim 11, in which a flexurally elastic hose is provided between the mask-holding part and the tube.

14. The nasal breathing mask of claim 13, in which the mask-holding part includes a tube connection piece over which the flexurally elastic hose is pushed to form a seal.

15. The nasal breathing mask of claim 14, in which a distance over which the flexurally elastic hose extends between the tube connection piece and the tube is approximately 2 mm.

16. The nasal breathing mask of claim 1, in which the mask part and forehead plate are formed of silicone.

17. The nasal breathing mask of claim 1, in which the positive engagement is a latching/clamping connection.

* * * * *

UNITED STATES PATENT AND TRADEMARK OFFICE
CERTIFICATE OF CORRECTION

PATENT NO. : 6,595,214 B1
DATED : July 22, 2003
INVENTOR(S) : Karl-Heinz Hecker et al.

It is certified that error appears in the above-identified patent and that said Letters Patent is hereby corrected as shown below:

<u>Title page,</u>
Item [73], Assignee, please delete "MPV-Truma Gesellschaft fur (DE)" and insert
-- MPV-Truma Gesellschaft für Medizintechnische Produkte GmbH (DE) --.

Signed and Sealed this

Second Day of March, 2004

JON W. DUDAS
*Acting Director of the United States Patent and Trademark Office*